United States Patent
Shih et al.

(10) Patent No.: US 8,642,666 B2
(45) Date of Patent: Feb. 4, 2014

(54) BIODEGRADABLE BLOCK COPOLYMERIC COMPOSITIONS FOR DRUG DELIVERY

(75) Inventors: Chung Shih, Sandy, UT (US); Gaylen M. Zentner, Salt Lake City, UT (US)

(73) Assignee: Protherics Salt Lake City, Inc., West Valley City, UT (US)

(*) Notice: Subject to any disclaimer, the term of this patent is extended or adjusted under 35 U.S.C. 154(b) by 424 days.

(21) Appl. No.: 12/490,968

(22) Filed: Jun. 24, 2009

(65) Prior Publication Data

US 2009/0264537 A1    Oct. 22, 2009

Related U.S. Application Data

(60) Division of application No. 10/186,462, filed on Jun. 28, 2002, now Pat. No. 7,649,023, and a continuation-in-part of application No. 10/167,768, filed on Jun. 11, 2002, now abandoned.

(51) Int. Cl.
| | | |
|---|---|---|
| A61K 47/14 | (2006.01) | |
| A61K 31/335 | (2006.01) | |
| C07D 305/00 | (2006.01) | |
| A61F 2/00 | (2006.01) | |
| A01N 25/00 | (2006.01) | |
| A01N 43/02 | (2006.01) | |

(52) U.S. Cl.
USPC ........ 514/772.1; 424/424; 424/425; 424/426; 424/486; 514/449; 514/511; 514/785

(58) Field of Classification Search
None
See application file for complete search history.

(56) References Cited

U.S. PATENT DOCUMENTS

| | | |
|---|---|---|
| 4,438,253 A | 3/1984 | Casey et al. |
| 4,526,938 A | 7/1985 | Churchill et al. |
| 4,534,899 A | 8/1985 | Sears |
| 4,652,441 A | 3/1987 | Okada et al. |
| 4,716,203 A | 12/1987 | Casey et al. |
| 4,745,160 A | 5/1988 | Churchill et al. |
| 4,830,855 A | 5/1989 | Stewart |
| 4,911,926 A | 3/1990 | Henry et al. |
| 4,938,763 A | 7/1990 | Dunn et al. |
| 4,942,035 A | 7/1990 | Churchill et al. |
| 4,960,790 A | 10/1990 | Stella et al. |
| 5,053,228 A | 10/1991 | Mori et al. |
| 5,100,669 A | 3/1992 | Hyon et al. |
| 5,123,912 A | 6/1992 | Kaplan et al. |
| 5,124,151 A | 6/1992 | Viegas et al. |
| 5,143,661 A | 9/1992 | Lawter et al. |
| 5,143,731 A | 9/1992 | Viegas et al. |
| 5,202,352 A | 4/1993 | Okada et al. |
| 5,260,066 A | 11/1993 | Wood et al. |
| 5,278,202 A | 1/1994 | Dunn et al. |
| 5,306,501 A | 4/1994 | Viegas et al. |
| 5,312,437 A | 5/1994 | Hermes et al. |
| 5,324,519 A | 6/1994 | Dunn et al. |
| 5,330,768 A | 7/1994 | Park et al. |
| 5,366,735 A | 11/1994 | Henry |
| 5,384,333 A | 1/1995 | Davis et al. |
| 5,410,016 A | 4/1995 | Hubbell et al. |
| 5,413,797 A | 5/1995 | Khan et al. |
| 5,514,380 A | 5/1996 | Song et al. |
| 5,538,739 A | 7/1996 | Bodmer et al. |
| 5,543,158 A | 8/1996 | Gref et al. |
| 5,560,933 A | 10/1996 | Soon-Shiong et al. |
| 5,599,552 A | 2/1997 | Dunn et al. |
| 5,607,686 A | 3/1997 | Totakura et al. |
| 5,612,052 A | 3/1997 | Shalaby |
| 5,626,862 A | 5/1997 | Brem et al. |
| 5,626,863 A | 5/1997 | Hubbell et al. |
| 5,631,015 A | 5/1997 | Bezwada et al. |
| 5,656,298 A | 8/1997 | Kitchell et al. |
| 5,681,576 A | 10/1997 | Henry |
| 5,683,723 A | 11/1997 | Spenlehauer et al. |
| 5,702,717 A * | 12/1997 | Cha et al. ................. 424/425 |
| 5,714,159 A | 2/1998 | Shalaby |
| 5,759,563 A | 6/1998 | Yewey et al. |
| 5,783,205 A | 7/1998 | Berggren et al. |
| 5,861,174 A | 1/1999 | Stratton et al. |
| 5,886,026 A | 3/1999 | Hunter et al. |
| 5,929,196 A | 7/1999 | Kissel et al. |
| 5,939,453 A | 8/1999 | Heller et al. |
| 5,981,568 A | 11/1999 | Kunz et al. |
| 6,001,395 A | 12/1999 | Coombes et al. |
| 6,004,573 A | 12/1999 | Rathi et al. |
| 6,117,949 A | 9/2000 | Rathi et al. |
| 6,136,333 A | 10/2000 | Cohn et al. |

(Continued)

FOREIGN PATENT DOCUMENTS

| | | |
|---|---|---|
| EP | 0092918 | 3/1983 |
| EP | 0258780 | 8/1987 |

(Continued)

OTHER PUBLICATIONS

Hirano et al. (Abstract of: Biopolymers 2012 97(2):117-22).*
European Search Report and Written Opinion for European Patent Application No. EP 09 00 9993, completed Sep. 3, 2010.
"Stabilization," *SSCI website*, Aug. 6, 2010 (available at http://www.ssci-inc.com/BiochemistryServices/Stabilization/tabid/95 /Default.aspx).
Bartoli, et al., "In vitro and in vivo antitumoral activity of free, and encapsulated taxol," *J. Microencapsulation* 7(2): 191-197 (1990).
Bauters, et al., "Angiopeptin Inhibits Oncogene Induction in Rabbit Aorta after Balloon Denudation," *Circulation*, 89(5): 2327-2331 (May 1994).

(Continued)

*Primary Examiner* — Ernst Arnold
(74) *Attorney, Agent, or Firm* — Hunton & Williams LLP

(57) ABSTRACT

An improved drug delivery composition and method of use is disclosed. The composition comprises one or more biodegradable block copolymer drug carriers; and a reconstitution enhancing and enabling agent comprising polyethylene glycol (PEG), a PEG derivative or a mixture of PEG and a PEG derivative. The composition can be administered as is or after being be dissolved or rapidly reconstituted in an aqueous vehicle to afford a homogeneous solution or uniform colloidal systems.

19 Claims, No Drawings

(56) References Cited

U.S. PATENT DOCUMENTS

| | | |
|---|---|---|
| 6,143,314 A | 11/2000 | Chandrashekar et al. |
| 6,201,065 B1 | 3/2001 | Pathak et al. |
| 6,201,072 B1 | 3/2001 | Rathi et al. |
| 6,287,588 B1 | 9/2001 | Shih et al. |
| RE37,410 E | 10/2001 | Brem et al. |
| 6,316,011 B1 | 11/2001 | Ron et al. |
| 6,322,805 B1 | 11/2001 | Kim et al. |
| 6,350,812 B1 | 2/2002 | Vert et al. |
| 6,413,539 B1 | 7/2002 | Shalaby |
| 6,544,544 B2 | 4/2003 | Hunter et al. |
| 6,551,610 B2 | 4/2003 | Shalaby et al. |
| 6,579,951 B1 | 6/2003 | Cohn et al. |
| 6,589,549 B2 | 7/2003 | Shih et al. |
| 6,592,899 B2 | 7/2003 | Fowers et al. |
| 6,616,941 B1 | 9/2003 | Seo et al. |
| 6,623,729 B2 | 9/2003 | Park et al. |
| 6,630,155 B1 | 10/2003 | Chandrashekar et al. |
| 6,730,334 B2 | 5/2004 | Zhao |
| 6,841,617 B2 | 1/2005 | Jeong et al. |
| 6,870,012 B2 | 3/2005 | Cohn et al. |
| 6,923,986 B2 | 8/2005 | Pathak et al. |
| 7,008,628 B2 | 3/2006 | Ron et al. |
| 7,018,645 B1 | 3/2006 | Piao et al. |
| 7,135,190 B2 | 11/2006 | Piao et al. |
| 7,153,520 B2 | 12/2006 | Seo et al. |
| 2002/0064559 A1 | 5/2002 | Lee et al. |
| 2002/0076441 A1 | 6/2002 | Shih et al. |
| 2002/0151650 A1 | 10/2002 | Pathak et al. |
| 2002/0173586 A1 | 11/2002 | Jeong et al. |
| 2002/0192285 A1 | 12/2002 | Mulye |
| 2003/0003074 A1 | 1/2003 | Zentner et al. |
| 2003/0031715 A1 | 2/2003 | Park et al. |
| 2003/0044467 A1 | 3/2003 | Brodbeck et al. |
| 2003/0068377 A1 | 4/2003 | Fowers et al. |
| 2003/0082234 A1 | 5/2003 | Seo et al. |
| 2003/0092776 A1 | 5/2003 | Ron et al. |
| 2003/0099709 A1 | 5/2003 | Shah et al. |
| 2003/0104347 A1 | 6/2003 | Mori et al. |
| 2003/0108610 A1 | 6/2003 | Flore et al. |
| 2003/0133979 A1 | 7/2003 | Burke et al. |
| 2003/0228366 A1 | 12/2003 | Shih et al. |
| 2004/0001872 A1 | 1/2004 | Shih et al. |
| 2004/0096508 A1 | 5/2004 | Gutowska et al. |
| 2004/0156906 A1 | 8/2004 | Ding et al. |
| 2004/0185101 A1 | 9/2004 | Shih et al. |
| 2004/0185104 A1 | 9/2004 | Piao et al. |
| 2004/0219214 A1 | 11/2004 | Gravett et al. |
| 2005/0008609 A1 | 1/2005 | Cohn et al. |
| 2005/0031669 A1 | 2/2005 | Shafiee et al. |
| 2005/0042295 A1 | 2/2005 | Hunter et al. |
| 2005/0058688 A1 | 3/2005 | Boerger et al. |
| 2005/0113531 A1 | 5/2005 | Chang et al. |
| 2005/0208137 A1 | 9/2005 | Hunter et al. |
| 2005/0238722 A1 | 10/2005 | Pathak et al. |
| 2005/0287196 A1 | 12/2005 | Cho et al. |
| 2006/0003008 A1 | 1/2006 | Gibson et al. |
| 2006/0013879 A9 | 1/2006 | Brodbeck et al. |
| 2006/0034888 A1 | 2/2006 | Pacetti et al. |
| 2006/0034899 A1 | 2/2006 | Ylitalo et al. |
| 2006/0034932 A1 | 2/2006 | Hunter et al. |
| 2006/0046960 A1 | 3/2006 | McKay et al. |
| 2006/0088515 A1 | 4/2006 | Higuchi et al. |
| 2006/0093639 A1 | 5/2006 | Starkebaum |
| 2006/0115532 A1 | 6/2006 | Shankar et al. |
| 2006/0188583 A1 | 8/2006 | Lim et al. |
| 2006/0193892 A1 | 8/2006 | Furst et al. |
| 2006/0251719 A1 | 11/2006 | Tabata |
| 2006/0292223 A1 | 12/2006 | Woolfson et al. |

FOREIGN PATENT DOCUMENTS

| | | | |
|---|---|---|---|
| EP | 0 737 703 | 10/1996 | |
| EP | 0 952 171 | 10/1999 | |
| JP | 02-078629 | 3/1990 | |
| WO | WO 92/12717 | 8/1992 | |
| WO | WO 93/24150 | 12/1993 | |
| WO | WO 95/03036 | 2/1995 | |
| WO | WO 01/12718 | * 2/2001 | ............ C08L 29/02 |
| WO | WO 01/45742 | 6/2001 | |
| WO | WO 01/82970 | 11/2001 | |
| WO | WO 02/102309 | 12/2002 | |
| WO | WO 03/103576 | 12/2003 | |

OTHER PUBLICATIONS

Fults, et al., "Sustained-Release of Urease from a Poloxamer Gell Matrix," *J. Parental Science & Technology*, 44(2): 58-65 (1009).

Imamura, "Sugar-Protein Interaction and Stabilization of Protein in Amorphous Sugar Matrix," *Cryobiology and Cryotechnology*, vol. 51, No. 1, pp. 31-35 (2005).

Johnston, et al., "Insulin Disposition Following Intramuscular Administration of an Insulin/Poloxamer Gel Matrix," *J. Parental Science and Technology*, 43(6): 279-289, (1989).

Johnston, et al., "Sustained Delivery of Interleukin-2 from a Poloxamer 407 Gel Matrix Following Intraperitoneal Injection in Mice," *Pharmaceutical Research*, vol. 9, No. 3 pp. 425-434 (1992).

Johnston, et al., "Toxicological Evaluation of Poloxamer Vehicles for Intramuscular Use," *J. Parental Science & Technology*, 39(2): 83-88 (1985).

Martini, et al., "Micellisation and Gelation of Triblock Copolymer of Ethylene Oxide and ∈-Caprolactone, CIE CL in Aqueous Solution," *J. Chem. Soc. Faraday Trans.*, vol. 90(13): 1961-1966 (1994).

Matsuda, et al., "Angiopeptin as a Potent Inhibitor of Myointimal Hyperplasia Systemic Injection and Local Administration via Impregnation in a Biodegradable Polymeric Gel," *ASAIO Journal*, p. M512-M517 (Jul. 1993).

Morikawa, et al., "Enhancement of Therapeutic Effects Recombinant Interleukin 2 on Transplantable Rat Fibrosarcoma by the Use of a Sustained Release Vehicle, Pluronic Gel," *Cancer Research*, 47: 37-41 (1987).

Sawhey, et al., "Bioerodible Hydrogels Based on Photopolymerized Poly(ethylene glyco)-co-poly(αhydroxy acid) Diacrylate Macromers," *Macromolecules*, 26 (1993).

Sawhney, et al., "Rapidly Degraded Terpolymers of dl-lactide, glycolide, and ∈-caprolactone with Increased Hydrophilicty by Copolymerization with Polyethers," *J. Biomedical Mat. Res.*, 24: 1397-1441 (1990).

Schott, Colloidal Dispersions, *Pharmaceutical Sciences*, Chapter 20, p. 266 (1980).

Walter, et al., "Interstital Taxol Delivered from a Biodegradable Polymer implant against Experimental malignant Glioma," *Cancer Research*, 54:2207-2212, Apr. 15, 1994.

Youxin, et al., "In-Vitro Degradation and Bovine Serum Albumin Release of the ABA Triblock Copolymers Consisting of poly(L(+)lactic acid) or poly (L(+) lactic acid-co-glycolic acid) A-blocks Attached to a Central Polyoxyethylene B-Blocks," *J. Controlled Release*, 32: 121-128 (1994).

Youxin, et al., "Synthesis and the Properties of Biodegradable ABA Triblock Copolymers Consisting of Poly(L-lactic acid) or poly(L-lactic-co-glycolic acid) A-blocks Attached to Central Poly(oxyethylene)B-Blocks," *J. Controlled Release*, 27: 247-257 (1994).

Final Office Action mailed Jun. 12, 2008 in co-pending U.S. Appl. No. 10/734,740.

Non-Final Office Action mailed Jul. 1, 2005 in co-pending U.S. Appl. No. 10/186,462.

Non-Final Office Action mailed Apr. 10, 2006 in co-pending U.S. Appl. No. 10/186,462.

Non-Final Office Action mailed Sep. 21, 2007 in co-pending U.S. Appl. No. 10/186,462.

Final Office Action mailed May 29, 2008 in co-pending U.S. Appl. No. 10/186,462.

\* cited by examiner

BIODEGRADABLE BLOCK COPOLYMERIC COMPOSITIONS FOR DRUG DELIVERY

CROSS-REFERENCE TO RELATED APPLICATIONS

This application is a divisional of U.S. patent application Ser. No. 10/186,462 filed Jun. 28, 2002, which is a continuation-in-part of U.S. patent application Ser. No. 10/167,768 filed Jun. 11, 2002, the contents of each are hereby incorporated by reference in their entirety.

FIELD OF THE INVENTION

The present invention relates to a composition for drug delivery. More specifically, the present invention relates to a copolymeric composition comprising a liquid polyethylene glycol (PEG), a PEG derivative or a mixture of PEG and PEG derivative; and a biodegradable block copolymeric drug carrier. Particularly, this invention relates to compositions comprising a to polyethylene glycol (PEG), PEG derivatives, or a mixture of a PEG and a PEG derivative, and biodegradable ABA, BAB and AB type block copolymers that are based on biodegradable hydrophobic polyester or poly(ortho ester) A blocks and hydrophilic polyethylene glycol (PEG) B blocks.

BACKGROUND OF THE INVENTION

Biodegradable polymers have been used as surgical sutures, wound dressings, and as drug delivery systems. Among them, polylactide (PLA), polyglycolide (PGA) and their copolymers (PLGA) have attracted the most attention. One example of a biodegradable polymeric drug delivery system is a system wherein a drug is contained in a biodegradable polymer matrix that is surgically implanted, which is a big disadvantage. In the form of injectable drug delivery systems, polymeric microspheres and nanospheres are known in the art. Commercially available drug delivery formulations based on PLGA microspheres include Lupron Depot® and Nutropin Depot®. Microsphere and nanosphere systems have disadvantages in that they require special and complex preparation methods. Unfortunately, manufacturing microsphere and nanosphere dosage forms requires use of toxic or dangerous solvents (e.g., methylene chloride, ethyl acetate) and elaborate procedures (e.g., double emulsions, or cryogenic spraying techniques). The batch size is usually small and the cost is high. In addition, since PLGA biodegradable polymers used can only be dissolved in organic solvents their preparation requires the use of such solvents which are foreign and harmful to the human body, and cannot be completely removed during manufacture by any known method. Furthermore, some drugs such as peptides and proteins may lose their pharmacological activity after contact with organic solvents.

An improvement to the aforementioned drug delivery systems is an in situ formed depot based on PLGA as disclosed in U.S. Pat. No. 5,599,552. In that system, PLGA is dissolved in water-soluble organic solvent(s), such as N-methyl-2-pyrrolidone, and the drug is either suspended or dissolved in this polymeric solution. The solution can be injected subcutaneously to form an in situ depot to trap the drug in the polymer that precipitates as the organic solvent diffuses away. However, the drawback is the requirement for an organic solvent that is used to dissolve the biodegradable PLGA polymer. Organic solvents, such as N-methyl-2-pyrrolidone, are foreign to the human body and can cause unwanted side effects both acutely and chronically.

U.S. Pat. No. 5,543,158 discloses nanoparticles or microparticles formed from a water-insoluble block copolymer consisting essentially of poly(alkylene glycol) and poly(lactic acid). The molecular weight of the block copolymer is high and the copolymer is insoluble in water. In the nanoparticle or microparticle, the biodegradable moieties of the copolymer are in the core of the nanoparticle or microparticle and the poly(alkylene glycol) moieties are on the surface of the nanoparticle or microparticle in an amount effective enough to decrease uptake of the nanoparticle or microparticle by the reticuloendothelial system. Nanoparticles are prepared by dissolving the block copolymer and drug in an organic solvent, forming an o/w emulsion by sonication or stirring, and collecting the nanoparticles containing the drug following precipitation.

Currently there are few synthetic or natural polymeric materials that can be used for the controlled delivery of drugs, including peptide and protein drugs, because of strict regulatory compliance requirements such as biocompatibility, low toxicity, having a clearly defined degradation pathway, and safety of the polymers and degradation products. The most widely investigated and advanced biodegradable polymers in regard to available toxicological and clinical data are the aliphatic poly($\alpha$-hydroxy acids), such as poly(D-, L-, or D, L-lactic acid) (PLA), poly(glycolic acid) (PGA) and their copolymers (PLGA). These polymers are commercially available and are presently used as bioresorbable sutures and in biodegradable microsphere drug delivery systems. FDA-approved microsphere systems for controlled release of leuprolide acetate (Lupron Depot™) and human growth hormone (Nutropin Depot™) are based on PLGA copolymers. Based on this history of use, PLGA copolymers have been the materials of choice in the initial design of parenteral controlled release drug delivery systems using a biodegradable carrier.

Even though there has been some limited success, biodegradable block copolymers that are based on biodegradable polyester or poly(ortho ester) and polyethylene glycol (PEG) blocks, when used as drug carriers, present problems that are associated with their physicochemical properties and attendant methods of fabrication. For example, biodegradable block copolymers are, by design, not stable in aqueous environments although shelf-lives of several years can be achieved when they are stored frozen. However, elimination of cold storage requirements would be advantageous in most instances. It is also desirable to gain further advantages related to rapid dissolution of neat block copolymers into aqueous vehicles at normal or ambient room temperature conditions. Rapid dissolution of the block copolymers permits reconstitution at time-of-use to occur, which in turn permits room temperature storage of neat block copolymers. Known water soluble block copolymers are slow to dissolve in water, often requiring several hours for complete dissolution to occur. Compositions that show accelerated dissolution kinetics are desired.

Some drugs, such as proteins, are stable in aqueous solutions for only short periods. To compensate for this short-term stability, these drugs are commonly formulated as dry cakes and powders that can be stored under water-free conditions for much longer periods. Immediately prior to administration the dry cake or powder is reconstituted with an aqueous vehicle. Thus the situation is frequently encountered where it is desirable to have both the drug and the block copolymer drug delivery system formulated in reconstitutable forms. To be facile, it is critical that reconstitution, i.e., dissolution of the block copolymers and drug be completed in a short period.

U.S. Pat. No. 5,384,333 discloses an injectable drug delivery composition in which a pharmacologically active substance is contained in a copolymer comprising a hydrophilic part and a hydrophobic part. However, the composition has to be heated to a relatively high temperature such as 38° C. to 52° C., immediately before use and it is difficult to uniformly distribute the drug in the polymeric composition. U.S. Pat. No. 5,612,052 discloses a block copolymer composition that when contacted with water forms a hydrogel. However, the drug incorporated in this composition is rapidly released. U.S. Pat. No. 5,599,552 discloses a composition wherein a water-insoluble biodegradable thermoplastic polymer is dissolved in a water-miscible organic solvent, and the resulting composition can be implanted where it then undergoes a phase transition when in contact with water or body fluids. However, the drawback is that it is difficult to use because a mono-molecular organic solvent is used to dissolve the biodegradable thermoplastic polymer. Most mono-organic solvents, such as N-methyl-2-pyrrolidone, ethyl lactate, dimethylsulfoxide, etc., cause side effects such as cell dehydration and tissue necrosis, etc. and they may also cause severe pain at the application sites.

U.S. Pat. No. 5,607,686 discloses a liquid polymeric composition prepared by mixing a hydrophilic liquid polymer, instead of a mono-molecular organic solvent, with a water-insoluble hydrophobic polymer. When contacted with water the composition undergoes a phase transition and forms an implant and thus it does not cause a the rapid volume reduction and it has no special side effects due to the good cytocompatibility of the low molecular weight polyethylene oxide. However, the water-insoluble hydrophobic polymers used are not biodegradable. In addition, the preparation of the composition requires heating to about 80° C. in order to achieve uniform mixing of the water-insoluble hydrophobic polymer and the hydrophilic liquid polymer. Therefore, this system may be suitable to use for adherence prevention and wound protection without any physiologically active substance, but it is not suitable for delivery of physiologically active substances, particularly peptide or protein medicines because peptide and protein medicines lose their activities at high temperatures. Furthermore, protein medicines are water soluble, thus it is very difficult to uniformly incorporate them into the composition. In addition, it is not disclosed in this patent how the drugs or physiologically active substances can be uniformly incorporated in the polymeric composition. Particularly, although polylactide, polyglycolide and their copolymers can be mixed with polyethylene glycol at high temperatures of 80° C. in order to obtain a uniform composition, the composition undergoes phase separation when it stands for a long period of time due the lowered affinity of the polylactide, the polyglycolide or their copolymers with polyethylene glycol. Therefore, it is very difficult to maintain a uniform composition.

Sterilization steps are necessary in the preparation of implant formulations. Existing sterilization methods are unsuitable for sustained drug delivery formulations due to properties of the implant compositions or because the methods are uneconomical or too complicated. For example, it is almost impossible to prepare a uniform solution by mixing a drug, a water-insoluble biodegradable polymer and a hydrophilic polymer. Therefore, the composition cannot be sterilized by simple methods such as membrane filtration. Furthermore, although the formulation may be prepared under sterilize conditions, such methods are very expensive to the extent that the practicability of the preparation may be lowered.

Therefore, there is a need for a biodegradable drug delivery composition that is a flowable liquid or can be rapidly reconstituted in an aqueous vehicle to afford a homogeneous true solution or uniform colloidal system in order to be easily prepared and administered to provide improved drug delivery. Accordingly, the present invention represents improved drug delivery compositions that minimize or are free of the problems mentioned above.

SUMMARY OF THE INVENTION

The present invention provides biodegradable compositions for drug delivery and is a flowable liquid or can be rapidly reconstituted in an aqueous vehicle to afford a homogeneous solution or uniform colloidal system, and methods of use thereof for preparing a pharmaceutically effective formulation for delivery of drugs.

The present invention also provides a method for preparing the biodegradable drug delivery composition and a method for effectively administering such a composition to warm blooded animals. The drug delivery composition of the present invention can be administered directly to a warm blooded animal without an aqueous vehicle, or can be administered after being rapidly reconstituted in an aqueous vehicle to afford a homogeneous solution or uniform colloidal system. The administration can be done by any functional means such as parenteral, ocular, inhalation, transdermal, vaginal, buccal, transmucosal, transurethral, rectal, nasal, oral, peroral, pulmonary, topical or aural and any other means of administration that may be compatible with the present invention.

The composition of the present invention comprises: 1) one or more biodegradable block copolymer drug carriers comprising A-B, A-B-A or B-A-B block, wherein the A block is a biodegradable polyester or poly(ortho ester) and the B block is polyethylene glycol (PEG) and the weight percentage of the A block is between 20% to 99%; and 2) a polyethylene glycol (PEG), a PEG derivative, or a mixtures of PEG and a PEG derivative, wherein the biodegradable drug carrier is soluble in the liquid PEG and/or PEG derivatives. The weight averaged molecular weight of the biodegradable block copolymer of the present invention is preferably within the range of 1,000 to 100,000 Daltons, more preferably within the range of 1,000 to 50,000 Daltons and most preferably within the range of 1,000 to 15,000 Daltons. Preferably, the weight percentage of the hydrophobic A block in the biodegradable block copolymer is between 20% to 99%, more preferably 20-85%.

One embodiment of the present invention is a composition comprises: 1) one or more biodegradable block copolymer drug carriers comprising A-B, A-B-A or B-A-B block copolymers, wherein the A block is a biodegradable polyester or poly(ortho ester) and the B block is polyethylene glycol (PEG), and 2) a polyethylene glycol (PEG), a PEG derivative, or a mixtures of PEG and a PEG derivative, wherein at least one of the biodegradable block copolymers is soluble in an aqueous solution and miscible with the PEG and/or PEG derivatives. Preferably, the biodegradable block copolymer drug carriers have a total molecular weight of 2000 to 8000 Daltons, and the weight percentage of the A block is between 50.1% to 83%. The polyethylene glycol (PEG), a PEG derivative, or a mixtures of PEG and a PEG derivative, preferably have a molecular weight of 150 to 1100 Daltons. The composition can be administered as is or after being be dissolved or rapidly reconstituted in an aqueous vehicle to afford a homogeneous solution or uniform colloidal system. After the administration, the water soluble biodegradable block copolymer may or may not form a gel, depending on molecular weight and hydrophobic block weight percentage of the block copolymer contained in the composition.

Another embodiment of the present invention is a liquid composition comprising 1) one or more biodegradable block copolymer drug carriers comprising A-B, A-B-A or B-A-B block copolymers, wherein the A block is a biodegradable polyester or poly(ortho ester) and the B block is polyethylene glycol (PEG), and 2) a liquid polyethylene glycol (PEG), a PEG derivative, or a mixtures of PEG and a PEG derivative; wherein the biodegradable block copolymer is insoluble in an aqueous solution but soluble in the PEG and/or PEG derivatives. Preferably, the water insoluble biodegradable block copolymer drug carriers have a total molecular weight of 1000 to 10,000 Daltons, and the weight percentage of the A block is between 20% to 99%. The liquid polyethylene glycol (PEG), a PEG derivative, or a mixtures of PEG and a PEG derivative, preferably have a molecular weight of 150 to 1100 Daltons. The liquid composition is a homogeneous solution or uniform colloidal system and can be administered directly to a warm blooded animal. After the administration, the liquid composition forms a drug containing depot and slowly releases the active substance over a prolonged period of time and is then decomposed into materials harmless to the human body and excreted.

Examples of suitable biodegradable water soluble drug carriers includes biodegradable ABA- or BAB-type triblock copolymers, or AB-type diblock copolymers based on biodegradable polyester or poly(ortho ester) A-blocks and hydrophilic B polymer block(s) consisting of polyethylene glycol (PEG). The biodegradable polyester are synthesized from monomers selected from the group consisting of D,L-lactide, D-lactide, L-lactide, D,L-lactic acid, D-lactic acid, L-lactic acid, glycolide, glycolic acid, s-caprolactone, 1,4-dioxan-2-one, s-hydroxy hexanoic acid, γ-butyrolactone, γ-hydroxy butyric acid, δ-valerolactone, δ-hydroxy valeric acid, hydroxybutyric acids, malic acid, and copolymers thereof.

Polyethylene glycol (PEG) is also sometimes referred to as poly(ethylene oxide) (PEO) or poly(oxyethylene) when incorporated into a block copolymer, and the terms can be used interchangeably for the purposes of this invention.

In the case where the A-block(s) are PLA/PLGA polyester, the lactate content is between about 20 to 100 mole percent, preferably between about 50 to 100 mole percent. The glycolate content is between about 0 and 80 mole percent, preferably between about 0 to 50 mole percent. Or, stated differently, when the A-block is PLGA the glycolate content is between about 1 and 80 mole percent and preferably between about 1 and 50 mole percent and the lactate content is between 20 and 99 mole percent and preferably between 50 and 99 mole percent.

The PEG derivative suitable in the present invention refers to an ester or ortho ester derivatized PEG having a molecular weight of 150 to 1100. Preferably, the ester derivatized PEG is a PEG derivatized from a member selected from the group consisting of D,L-lactide, D-lactide, L-lactide, D,L-lactic acid, D-lactic acid, L-lactic acid, glycolide, glycolic acid, ε-caprolactone, 1,4-dioxan-2-one, ε-hydroxy hexanoic acid, γ-butyrolactone, γ-hydroxy butyric acid, δ-valerolactone, δ-hydroxy valeric acid, hydroxybutyric acids, malic acid, and mixtures thereof. The PEG derivative can also be a member represented by $R^1-CO-O-(CH_2-CH_2-O)_n-CO-R^2$ or $R^1-O-(CH_2-CH_2-O)_n-R^2$ wherein $R^1$ and $R^2$ are independently members selected from the group consisting of H and $C_1$ to $C_{10}$ alkyl and n is an integer between 3 and 20.

The biodegradable block copolymer drug carriers suitable for the present invention can form homogeneous, free-flowing solutions or uniform colloidal systems in an aqueous vehicle or in the liquid PEG or PEG derivatives or mixtures thereof. Homogeneous solutions and uniform colloidal systems of the drug delivery compositions includes all flowing forms of the compositions of the present invention, with or without water, drug(s), and any additives or excipients as necessary to prepare formulations that are pharmaceutically and therapeutically useful. The drug may be present as either a true solution or in a colloidal state such as emulsion or a suspension. All forms can act to facilitate administration of the drug and enhance the therapeutic effect. Such therapeutic effects may be optimized by controlling the copolymer molecular weights, compositions, and the relative ratios of the hydrophilic and hydrophobic blocks, ratios of drug to copolymer, ratios of copolymer to PEG and/or PEG derivatives, and both drug and copolymer concentrations in the final administered dosage form. Additional advantages of this invention will become apparent from the following detailed description of the various embodiments.

DETAILED DESCRIPTION OF THE INVENTION

This invention is not limited to the particular configurations, process steps, and materials disclosed herein, as such configurations, process steps, and materials may vary somewhat. It is also to be understood that the terminology employed herein is used for the purpose of describing particular embodiments only, and is not intended to be limiting since the scope of the present invention will be limited only by the appended claims and equivalents thereof.

In this specification and the appended claims, the singular forms "a," "an," and "the" include plural references unless the context clearly dictates otherwise. Thus, for example, reference to a composition for delivering "a drug" includes reference to one, two, or more drugs. In describing and claiming the present invention, the following terminology will be used in accordance with the definitions set out below.

"Effective amount" means an amount of a drug, biologically active agent or pharmacologically active agent that provides the desired local or systemic effect.

"Copolymer solution", when used in reference to a biodegradable block copolymer contained in such a solution, shall mean an aqueous composition having such biodegradable block copolymer drug carrier either dissolved to form a homogeneous solution or uniform colloidal system.

"Drug formulations", "drug delivery compositions", and the like, shall mean the combination of drug, the block copolymer drug carrier, and PEG, PEG derivatives, or mixtures of PEG and PEG derivatives. They shall include all combinations of the drug with the block copolymer and PEG, PEG derivatives, or mixtures thereof.

"Aqueous solution", "aqueous vehicle" and the like, shall include water without additives or aqueous solutions containing additives or excipients such as pH buffers, components for tonicity adjustment, antioxidants, preservatives, drug stabilizers, etc., as commonly used in the preparation of pharmaceutical formulations.

"Drug solution", "solubilized drug", "dissolved drug" and all other terms that refer to the drug in a solution or dissolved state includes the drug being present as either a homogeneous solution, micellar solution, or in a colloidal state such as emulsion or a suspension. Thus, solubilized drugs and drug solutions include all flowing forms of the drug delivery compositions of the present invention. All forms can act to facilitate administration of the drug and enhance the therapeutic to effect.

"Reconstitution" refers to mixing of biodegradable block copolymer drug carriers and the PEG, PEG derivatives or mixtures thereof with an aqueous solvent system to create a homogenous solution or uniform colloidal system. This is in addition to the more traditional definition of reconstitution where drug and excipients are mixed with a solvent, usually aqueous, immediately before administration.

"Enhanced reconstitution properties" refers to properties that enable rapid reconstitution of block copolymeric drug carriers to the final physical state as either a true solution or a uniform colloidal system. The reconstitution process occurs within a short period of time, typically between 0.01 minutes to 120 minutes, preferably within 0.01 minutes to 60 minutes, and most preferably within 0.01 minutes to 30 minutes.

"Reverse thermal gelation" is the phenomenon whereby an aqueous solution of a block copolymer spontaneously increases in viscosity, and in many instances transforms into a semisolid gel, as the temperature of the polymer solution is increased above the gelation temperature of the block copolymer solution. For the purpose of the invention, the term gel includes both the semisolid gel state and the high viscosity state that exists above the gelation temperature. When cooled below the gelation temperature the gel spontaneously reverses to reform the lower viscosity polymer solution. This cycling between the solution and the gel may be repeated indefinitely because the sol/gel transition does not involve any change in the chemical composition of the polymer solution. All interactions to create the gel are physical in nature and do not involve the formation or breaking of covalent bonds.

"Administration" is the means by which drug formulations are presented to humans and other warm-blooded animals in effective amounts, and includes all routes for dosing or administering drugs, whether self-administered or administered by medical practitioners.

"Parenteral" shall mean administration by means other than through the digestive tract such as by intramuscular, intraperitoneal, intra-abdominal, subcutaneous, intrathecal, intrapleural, intravenous and intraarterial means.

"Depot" means a localized site in the body containing concentrated active agents or drugs. Examples of formulations that form depots are gels, implants, microspheres, matrices, particles, etc.

"Biodegradable" means that the block copolymer or oligomer can chemically break down or degrade within the body to form nontoxic components. The rate of degradation can be the same or different from the rate of drug release.

"Drug" shall mean any organic or inorganic compound or substance having biological or pharmacological activity that can be adapted or used for a therapeutic purpose.

"Peptide," "polypeptide," "oligopeptide" and "protein" shall be used interchangeably when referring to peptide or protein drugs and shall not be limited as to any particular molecular weight, peptide sequence or length, field of bioactivity or therapeutic use unless specifically stated.

"PLGA" shall mean a copolymer or copolymer radicals derived from the condensation copolymerization of lactic acid and glycolic acid, or, by the ring opening copolymerization of lactide and glycolide. The terms lactic acid and lactate are used interchangeably; glycolic acid and glycolate are also used interchangeably.

"PLA" shall mean a polymer derived from the condensation of lactic acid or by the ring opening polymerization of lactide.

"PGA" shall mean a polymer derived from the condensation of glycolic acid or by the ring opening polymerization of glycolide.

"Biodegradable polyester or poly(ortho ester)s" refers to any biodegradable polyester or poly(ortho ester)s. The polyesters are preferably synthesized from monomers selected from the group consisting of D,L-lactide, D-lactide, L-lactide, D,L-lactic acid, D-lactic acid, L-lactic acid, glycolide, glycolic acid, ε-caprolactone, 1,4-dioxan-2-one, ε-hydroxy hexanoic acid, γ-butyrolactone, γ-hydroxy butyric acid, δ-valerolactone, δ-hydroxy valeric acid, hydroxybutyric acid, malic acid, and mixtures thereof.

"Ortho ester" is a carbon which single bonded to three oxygen atoms covalently.

The present invention is based on the discovery of PEG, PEG derivatives or mixtures thereof that can, in minutes, efficiently accelerate the dissolution of the biodegradable block copolymer drug carriers into an aqueous medium. The liquid PEG, PEG derivatives or mixtures thereof of the present invention can also dissolve the biodegradable block copolymer drug carriers to create a flowable drug delivery composition. The "PEG, PEG derivatives or mixtures thereof" of the present invention have a weight averaged molecular weight of 150 to 1100. The PEG derivative suitable in the present invention refers to an ester or ortho ester derivatized PEG having a molecular weight of 150 to 1100. Preferably, the ester derivatized PEG is a PEG derivatized from a member selected from the group consisting of D,L-lactide, D-lactide, L-lactide, D,L-lactic acid, D-lactic acid, L-lactic acid, glycolide, glycolic acid, ε-caprolactone, 1,4-dioxan-2-one, ε-hydroxy hexanoic acid, γ-butyrolactone, γ-hydroxy butyric acid, δ-valerolactone, δ-hydroxy valeric acid, hydroxybutyric acids, malic acid, and mixtures thereof. The PEG derivative can also be a member represented by $R^1$—CO—O—$(CH_2$—$CH_2$—O$)_n$—CO—$R^2$ or $R^1$—O—$(CH_2$—$CH_2$—O$)_n$—$R^2$ wherein $R^1$ and $R^2$ are independently members selected from the group consisting of H and $C_1$ to $C_{10}$ alkyl and n is an integer between 3 and 20.

The biodegradable block copolymer drug carriers of the present invention may be soluble in an aqueous solution, in the liquid PEG, PEG derivatives or mixtures thereof, or both. Examples of some of these biodegradable block copolymer drug carriers are disclosed in U.S. Pat. No. 6,201,072 and pending U.S. patent application Ser. Nos. 09/559,799; 09/971,074, filed on Oct. 3, 2001 and 09/971,082 filed on Oct. 3, 2001, hereby fully incorporated by reference. The composition can be administered as is or after being dissolved or rapidly reconstituted in an aqueous vehicle to afford a homogeneous solution or uniform colloidal system. After the administration, the water soluble biodegradable block copolymer may or may not form a gel, depending on molecular weight and hydrophobic block weight percentage of the block copolymer contained in the composition. Water soluble biodegradable block copolymers are prepared wherein the hydrophilic B-block(s) make up about 17 to 49.9% by weight of the copolymer and the hydrophobic A-block or blocks make up about 50.1 to 83% by weight of the copolymer. The weight ratio of the water soluble biodegradable block copolymer drug carrier and the PEG, PEG derivatives, or mixtures of PEG and PEG derivatives, is between 5:1 and 1:99. This composition can be administered as is or after being quickly reconstituted in water or an aqueous solution and form a polymer solution comprising the composition of the present invention in water or the aqueous solution at a weight ratio between 2:1 and 1:10000.

Alternatively, the biodegradable block copolymer may be insoluble in an aqueous solution but is soluble in the liquid polyethylene glycol, PEG derivatives or mixtures thereof. In this case, the liquid composition is a homogeneous solution or uniform colloidal system and can be administered directly to a warm blooded animal. After the administration, the liquid composition forms a drug containing depot and slowly releases the active substance over a prolonged period of time and is then decomposed into materials harmless to the human body and excreted. In the liquid composition of the present invention, the weight ratio of the biodegradable block copolymer to the PEG, PEG derivatives or mixtures thereof is preferably within the range of 5:1 to 1:99, and more preferably within the range of 2:1 to 1:99 and most preferably within the range of 1:2 to 1:5.

In one embodiment, the biodegradable drug carrier comprises ABA-type or BAB-type triblock copolymers, AB-type diblock copolymers or mixtures thereof, where the A-blocks are relatively hydrophobic and comprises a biodegradable polyester or poly(ortho ester), and the B-blocks are relatively hydrophilic and comprises polyethylene glycol (PEG), said copolymer having a hydrophobic content of between 50.1 to 83% by weight and hydrophilic content of between 17 to 49.9% by weight, and an overall block copolymer molecular weight of between 2000 and 8000. The drug carriers exhibit water solubility at temperatures below normal mammalian body temperatures and undergoes reversible thermal gelation to then exist as a gel at temperatures equal to physiological mammalian body temperatures.

In another embodiment, the biodegradable drug carrier is an ABA-type, BAB-type, or AB-type block copolymer, or mixtures thereof, where the A-blocks are relatively hydrophobic and comprises a biodegradable polyester or poly(ortho ester), and the B-blocks are relatively hydrophilic and comprises polyethylene glycol (PEG), said block copolymer having a hydrophobic content of between 50.1 to 65% by weight and a hydrophilic content of between 35 to 49.9% by weight, and an overall block copolymer weight-averaged molecular weight of between 2400 and 4999. The drug carriers are water soluble and capable of enhancing the solubility of drugs, hydrophobic drugs in particular, in water, to form a drug solution.

In still another embodiment, the polymeric drug carrier comprises biodegradable polyester or poly(ortho ester) oligomers, and particularly PLA/PLGA oligomers having a weight averaged molecular weight of between 400 and 10,000, mixed with biodegradable ABA-type or BAB-type triblock copolymers, or AB-type diblock copolymers having a weight averaged molecular weight of between 2400 and 4999. The block copolymers have 50.1 to 65% by weight of the hydrophobic A block(s) comprising biodegradable polyester or poly(ortho ester)s and 35 to 49.9% by weight of the hydrophilic B block(s) consisting of polyethylene glycol (PEG).

The PEG, PEG derivatives or mixtures thereof used in the present invention dissolves or uniformly mixes with the biodegradable block copolymer and so reduces the viscosity and increases the fluidity of the composition. The compositions of the present invention are flowable liquids or can be easily formulated with an aqueous vehicle to afford a fluid homogeneous solution or uniform colloidal system. In the cases that the block copolymeric drug carrier is insoluble in an aqueous vehicle but soluble in the liquid PEG and/or PEG derivatives, when in contact with water or body fluids, the block copolymer forms a drug depot. In cases that the block copolymeric drug carrier is soluble in an aqueous vehicle and miscible with the PEG and/or PEG derivatives, the composition can be easily administered as is or reconstituted with an aqueous vehicle. After the administration, the block copolymer drug carrier may or may not form a drug depot. Therefore, the liquid PEG, PEG derivative or mixtures thereof of the present invention should be a material that does not cause loss of activity of the physiologically active substance.

For purposes of disclosing molecular weight parameters, all reported molecular weight values are based on measurements by $^1$H-NMR or GPC (gel permeation chromatography) analytical techniques. The reported weight averaged molecular weights and number averaged molecular weights were determined by GPC and $^1$H-NMR, respectively. The reported lactide/glycolide ratios were calculated from $^1$H-NMR data. GPC analysis was performed on a Styragel HR-3 column, or equivalent, calibrated with PEG standards using RI detection and chloroform as the eluent, or on a combination of Phenogel, mixed bed, and 500 Å columns calibrated with PEG standards using RI detection and tetrahydrofuran as the eluent for the ABA and BAB triblock copolymers.

ABA-type and BAB-type triblock copolymers, and AB-type diblock copolymers may be synthesized by ring opening polymerization, or condensation polymerization. Additionally, the B-blocks may, in certain instances, be coupled to the A-blocks by ester or urethane links and the like. Condensation polymerization and ring opening polymerization procedures may be utilized as may the coupling of a monofunctional hydrophilic B block to either end of a difunctional hydrophobic A block in the presence of coupling agents such as isocyanates. Furthermore, coupling reactions may follow activation of functional groups with activating agents, such as carbonyl diimidazole, succinic anhydride, N-hydroxy succinimide, p-nitrophenyl chloroformate and the like.

The hydrophilic B-block is formed from PEG of an appropriate molecular weight. PEG was chosen as the hydrophilic B-block because of its unique biocompatibility, nontoxic properties, hydrophilicity, solubilization properties, and rapid clearance from a patient's body. The hydrophobic A-blocks are utilized because of their biodegradable, biocompatible, and solubilization properties. The in vitro and in vivo degradation of hydrophobic, biodegradable polyester or poly(ortho ester) A-blocks are well understood and the degradation products are readily metabolized and/or eliminated from the patient's body.

Drugs that may be incorporated with the drug delivery compositions of the present invention can be any bioactive agent, but particular advantage is achieved with bioactive agents having limited solubility or dispersibility in an aqueous or hydrophilic environment, or any bioactive agent that requires enhanced solubility or dispersibility. Without limiting the scope of the present invention, suitable drugs include those drugs presented in current edition of Goodman and Gilman's "The Pharmacological Basis of Therapeutics" or the current edition of The Merck Index. Both volumes list drugs suitable for numerous types of therapeutic applications, including drugs in the following categories:drugs acting at synaptic and neuroeffector junctional sites, drugs acting on the central nervous system, drugs that influence inflammatory responses, drugs that affect the composition of body fluids, drugs affecting renal function and electrolyte metabolism, cardiovascular drugs, drugs affecting gastrointestinal function, drugs affecting uterine motility, chemotherapeutic agents for parasitic infections, chemotherapeutic agents for microbial diseases, antineoplastic agents, immunosuppressive agents, drugs affecting the blood and blood-forming organs, hormones and hormone antagonists, dermatological agents, heavy metal antagonists, vitamins and nutrients, vaccines, oligonucleotides and gene therapies.

Incorporating one or more drugs mentioned in the above categories with the compositions of the present invention to form drug delivery compositions which can be dissolved or easily reconstituted to form an aqueous solution or uniform colloidal system can be achieved by simply adding the drug to the liquid composition or an aqueous solutions of the compositions of the present invention, or by mixing the drug with the compositions of the present invention and thereafter adding water or an aqueous solution to form a solution or uniform colloidal system.

Mixtures of the compositions of the present invention with peptide/protein drugs, and/or other types of drugs, may be prepared as flowable drug delivery formulations or formulations that may be easily reconstituted in the form of a solution or dispersion. The flowable formulation is then administered parenterally, topically, transdermally, transmucosally, inhaled, or inserted into a cavity such as by ocular, vaginal, transurethral, rectal, nasal, oral, peroral, buccal, pulmonary or aural administration to a patient. Many of the solubilized drug formulations prepared by implementing the present invention may be diluted in an i.v. bag or by other means, and administered to a patient for an extended period, without precipitation of the drug. Due to the biocompatibility of the materials and the free flowing nature of the system at physiological temperatures, this system will cause minimal toxicity and minimal mechanical irritation to the surrounding tissue.

A distinct advantage to the compositions of this invention lies in the ability of PEG, PEG derivatives or mixtures thereof to reduce the viscosity of the biodegradable block copolymer drug carriers into a form that is flowable liquid or can be quickly reconstitutable in water or an aqueous solution to form a solution or uniform colloidal system for drug delivery. In one possible configuration, a dosage form comprised of a solution of the block copolymer drug carrier and a PEG, PEG derivatives or mixtures thereof that contains drug is administered to the body. In another possible configuration, the drug delivery composition of the present invention may be quickly dissolved or reconstituted by using water or other aqueous solutions.

The only limitation as to how much drug can be dissolved or dispersed in the drug delivery composition of the present invention is one of functionality, namely, the drug:copolymer ratio may be increased until the properties of the mixture are adversely affected to an unacceptable degree, or until to the properties of the system are adversely affected to such a degree as to make administration of the system unacceptably difficult. Generally speaking, it is anticipated that in most instances where dissolution is desired, the drug will be present at between about $10^{-6}$ to about 100 percent by weight of the combined weight the block copolymer drug carrier and the PEG, PEG derivatives or mixtures thereof, with ranges of between about 0.001% to 25% by weight being the most common. For example, having the drug present at 100% by weight of the combined weight of the block copolymer drug carrier and the PEG, PEG derivatives or mixtures thereof means that the drug and combined weight the block copolymer drug carrier and the PEG, PEG derivatives or mixtures thereof are present in equal amounts (i.e., equal weights). Generally speaking, it is anticipated that in most instances where dispersion is desired, the upper drug:copolymer ratio could substantially exceed the range noted above for dissolution. These ranges of drug loading are illustrative and will include most drugs that may be utilized in the present invention. However, such ranges are not limiting to the invention should drug loadings outside this range be functional and effective.

The present invention thus provides compositions comprising biodegradable block copolymer drug carriers and PEG, PEG derivatives or mixtures thereof that are flowable liquids or can be rapidly reconstituted in an aqueous vehicle to afford useful forms that may be either homogeneous true solutions or uniform colloidal systems. The drug solution formed with the drug delivery compositions of the present invention has desirable physical stability, therapeutic efficacy, and toxicology. The PEG, PEG derivatives or mixtures thereof of the present invention can be used for water soluble or water insoluble block copolymeric drug carriers, particularly for biodegradable di- or triblock copolymers that have reverse gelation properties and/or polymers that can enhance the solubility of drugs, especially hydrophobic drugs.

The following are examples that illustrate preferred embodiments of the invention but are intended as being representative only.

Example 1

PEG-300 (107.6 g) was placed in a 250-mL round bottom flask and dried under vacuum (0.2 torn, 90° C.) for 3 hours. D,L-Lactide (33.4 g) and glycolide (9.0 g) was added and the head-space was replaced by dried nitrogen. The mixture was brought to 135° C. and the reaction was initiated by adding stannous octoate (20 mg) via a dry syringe. The reaction mixture was allowed to stir under dry nitrogen at 155° C. for four additional hours. Residual monomers were removed under vacuum (0.2 torr, 90° C., 2 hr). The resulting PEG derivative (D1) was a clear free-flowing liquid.

Example 2

Following the procedure described in Example 1, the following PEG derivatives were prepared.

TABLE 1

PEG derivatives synthesized by the method described in Example 1

| ID | PEG | PEG weight (gram) | Glycolide (gram) | D,L-Lactide (gram) |
|---|---|---|---|---|
| D2 | PEG200NF | 30.0 | 7.62 | 28.38 |
| D3 | PEG200NF | 33.33 | 5.64 | 21.02 |
| D4 | PEG300NF | 57.14 | 4.84 | 18.02 |
| D5 | PEG600NF | 50.0 | 4.23 | 15.75 |
| D6 | Triethylene glycol | 50.0 | 4.23 | 15.77 |
| D7 | PEG300NF | 50.25 | 19.75 | — |
| D8 | PEG300NF | 86.15 | 24.67 | 9.19 |
| D9 | PEG300NF | 100.5 | — | 39.5 |

Example 3

PEG-300 (40 g) was placed in a 250-mL round bottom flask. Moisture was removed by drying under vacuum (0.2 torr) at 90° C. for 3 hours. Acetic anhydride (30 g) was added and the reaction mixture was brought to reflux under nitrogen over 48 hours. Excess acetic anhydride was removed by vacuum distillation at 100° C. for 24 hours. The resulting PEG derivative (D10) was a clear, free-flowing liquid.

Example 4

This example illustrates the synthesis of the ABA-type triblock copolymer PLGA-PEG-PLGA by ring opening copolymerization.

PEG 1000 NF (65.3 g) and PEG 1450 NF (261 g) was dried under vacuum (1 mmHg) at 130° C. for 5 hours. D, L-Lactide (531.12 g) and glycolide (142.6 g) were added to the flask and heated to 155° C. to afford a homogenous solution. Polymerization was initiated by the addition of 250 mg stannous octoate to the reaction mixture. After maintaining the reaction for five hours at 145° C., the reaction was stopped and the flask was cooled to room temperature. Unreacted lactide and glycolide were removed by vacuum distillation. The resulting PLGA-PEG-PLGA copolymer mixture (ABA 1) had a weight averaged molecular weight (Mw) of 4255 as measured by GPC. This triblock copolymer mixture is water soluble at room temperature. A 23% by weight aqueous solution of this triblock copolymer mixture had a gel temperature between 30° C. and 37° C.

Example 5

Using the procedure described in Example 4, the following copolymers or copolymer mixtures were synthesized:

TABLE 2

Copolymers synthesized using the procedure described in Example 3

| Block Copolymer | LA/GA Molar Ratio | PEG1 MW | PEG2 MW | PEG1/ PEG2 wt Ratio | MW (Dalton) | Remarks |
|---|---|---|---|---|---|---|
| PLG-PEG-PLG (ABA 2) | 75/25 | 1000 | — | 100/0 | 4250 | Water soluble |
| PLG-PEG-PLG (ABA 3) | 75/25 | 1450 | — | 100/0 | 3950 | Water soluble |
| PLA-PEG-PLA (ABA 4) | 100/0 | 1000 | 1450 | 10/90 | 3980 | Water soluble |
| PLG-PEG-PLG (ABA 5) | 75/25 | 1450 | — | 100/0 | 7540 | Water insoluble |
| PLA-PE-PLA (ABA 6) | 100/0 | 1000 | 600 | 80/20 | 6500 | Water insoluble |

Example 6

AB diblock copolymer was synthesized by placing 25.7 g of PEG-Me (Mw: 2000) in a 250 mL 3-neck round bottom reaction flask. Water was removed by heating in an oil bath (155° C.) under vacuum (0.5 torr) for 3 hours. The reaction flask was then raised out of the oil bath and the vacuum was released.

D,L-Lactide (32.0 g) was weighed and added to the reaction flask. The headspace was replaced with dry nitrogen by repeated evacuation and flushing with dry nitrogen 5 times.

The flask was then lowered and immersed in a 155° C. oil bath. Once the content was melted and the internal temperature reached 150° C., 2 drops (200 ppm) of stannous 2-ethylhexanoate was added to initiate the polymerization. The reaction mixture was stirred using an overhead stirrer for 8 hours at a rate of 100-200 rpm. The temperature was then reduced to 140° C., and the residual monomer was removed under reduced pressure (<1 torr) over 1 hour. The residue is a translucent, off-white solid having a molecular weight of 5450.

One gram of the diblock copolymer was added to 4 grams of PEG derivative (D10) to afford a clear and free flowing liquid. Upon addition of the mixture to 37° C. water, the mixture turned cloudy due to apparent precipitation of the water insoluble diblock copolymeric component.

Example 7

Me-PEG (MW 550; 48.6 g) was transferred into a 250 mL 3-neck round bottom reaction flask. The oil bath was heated to 100° C. The molten PEG-Me was stirred under vacuum for 5 hours to remove water. The reaction flask was then raised outside of the oil bath and the vacuum was released. D,L-Lactide (97.68 g) and glycolide (26.47 g) were weighed and added the reaction flask. The headspace was replaced with dry nitrogen. The flask was then immersed into a 155° C. oil bath. Once the D,L-lactide was melted and the temperature inside the reaction flask reached 150° C., 2 drops (200 ppm) of stannous 2-ethylhexanoate was added to the reaction flask. The reaction was stirred continuously for 8 hours at a rate of 100-150 rpm.

The oil bath temperature was reduced to 140° C. and the reaction flask was attached to vacuum (<1 torr) for an hour to remove residual monomer. The diblock copolymer had honey-like consistency with molecular weight of 2010. The residue (145 g) was added to 1,6-diisocynatohexane (6.06 g) via an oven dried syringe and the reaction mixture was allowed to stir at 140° C. for 2 additional hours. The residue was purified by dissolving the polymer in water and precipitation at 70° C. Water was removed by lyophilization and the residual BAB triblock copolymer had a molecular weight of 4250.

One gram of the polymer was dissolved in 4 gram of PEG derivative (D 4) and the mixture was added to 25 mL of warm water (37° C.) via a 24-G needle. Upon addition of the mixture to 37° C. water, the mixture turned cloudy due to apparent precipitation of the water insoluble diblock copolymeric component.

Example 8

The use PEG derivatives for reconstitution are illustrated in this example.

The PEG derivative (1.5 g) prepared from Example 1 were added to 1 gram of PLGA-PEG-PLGA triblock copolymer prepared from Example 4. The two components were intimately mixed into a homogeneous mixture. To the mixture, water for injection (5 g) was added shaken. The mixture took 1 minute to reconstitute. The resulting aqueous solution had a gelation temperature at 30° C. and 37° C.

Zinc insulin (5 mg) was reconstituted with 5 mL of the aqueous solution and the solution was injected into 37° C. water. The solution rapidly gelled.

Example 9

Zn-insulin (5 mg) is suspended a mixture composed of a triblock copolymer (ABA 6; 1 g) dissolved in 6 g of PEG derivative (D 2). The mixture is a free-flowing liquid. One mL of the suspension is injected into warm water (25 mL; 37° C.). Upon addition of the mixture to 37° C. water, the mixture turned cloudy due to apparent precipitation of the water insoluble triblock copolymeric component.

Example 10

The PEG derivatives (D6; 4 g) were added to 1 gram of PLGA-PEG-PLGA triblock copolymer (ABA3). Also added to the mixture was 50 mg of paclitaxel. The mixture was intimately mixed into a homogeneous mixture at ca. 40° C. for ca. 20 minutes. The mixture was a clear free flowing liquid. One gram of the mixture was added to a beaker containing 25 mL of warm water (37° C.). The mixture apparently dissolved rapidly to afford a clear solution or uniform colloid.

Example 11

The PEG derivative (3 g) from Example 1 were intimately mixed with 1 gram of PLGA-PEG-PLGA triblock copolymer (ABA3) and 0.08 g of poly(D,L-lactate-co-glycolate) (MW 1200) into a homogeneous mixture. Paclitaxel (75 mg) was dissolved into the mixture with gentle stirring at ca. 45° C. After equilibrated to ambient temperature, water for injection (5 g) was added and the mixture was shaken. The mixture apparently dissolved rapidly to afford a clear solution or uniform colloid.

Example 12

This example illustrate the synthesis of poly(ortho ester) AB diblock copolymer.

Dried 1,4-cyclohexanedimethanol (2.6 g), PEG 2000 methyl ether (4 g) is heated at 70° C. with DETOSU (3,9-bis (ethylidene)-2,4,8,10-tetraoxaspiro[5,5]undecane; 4.35 g) in dried 1,4-dioxane (100 mL) over 8 hour. The solvent is removed under vacuum (0.5 torr; 70° C.) over 40 hours. The resulting poly(ortho ester) AB diblock copolymer is a transparent copolymer.

Example 13

This example illustrates the synthesis of PEG ortho ester derivative. PEG 300 (25.0 g) is heated in a round bottomed flask under vacuum at 90° C. for 3 hours to remove residual water. Molten DETOSU (3,9-bis(ethylidine)-2,4,8,10-tetraoxaspiro[5,5]undecane) (4.0 grams) is added to the flask through an oven dried syringe. The mixture is allowed to heat at 90° C. over 5 hours. The resulting PEG ortho ester derivative is a clear liquid.

Example 14

This example illustrates the use of PEG ortho ester derivative. Paclitaxel (50 mg) is dissolved with mild heating into a mixture of PEG derivative (15 g) synthesized in Example 13 and an AB diblock poly(ortho ester) copolymer (3 g) prepared in Example 12. The resulting mixture is a clear liquid. Upon addition of the mixture to 37° C. water, the mixture turned cloudy due to apparent precipitation of the water insoluble diblock copolymeric component.

The above description will enable one skilled in the art to make a composition comprising biodegradable block copolymer drug carriers and PEG, PEG derivatives, or a mixtures thereof, said composition is a flowable liquid or can be rapidly reconstituted in an aqueous vehicle to homogeneous solutions or uniform colloidal systems. Although the drug delivery compositions are described to show the functionality of the compositions of the present invention, these descriptions are not intended to be an exhaustive statement of all drug carriers that can be rendered soluble and/or constitutable by the compositions of the present invention. Certainly, numerous other drug carriers or drugs from various categories of therapeutic agents are well suited for the drug delivery compositions described in this invention. It will be immediately apparent to one skilled in the art which various modifications may be made without departing from the scope of the invention that is limited only by the following claims and their functional equivalents.

We claim:

1. A composition comprising:
(a) one or more biodegradable block copolymer drug carriers comprising A-B, A-B-A or B-A-B block copolymers having a total weight average molecular weight of 2000 to 4990 Daltons, wherein the A block is a biodegradable polyester or poly(ortho ester) and the B block is polyethylene glycol (PEG), and the weight percentage of the A block is between 51% to 83% and the weight percentage of the B block is between 17% to 49%; and
(b) a polyethylene glycol (PEG), a PEG derivative, or a mixture of PEG and a PEG derivative, said PEG or PEG derivative having a molecular weight of 150 to 1100 Daltons, wherein the PEG derivative is an ester derivatized PEG and wherein the PEG is derivatized with D,L-lactide, D-lactide, L-lactide, D,L-lactic acid, D-lactic acid, L-lactic acid, glycolide, glycolic acid, $\epsilon$-caprolactone, 1,4-dioxan-2-one, $\epsilon$-hydroxy hexanoic acid, $\gamma$-butyrolactone, $\gamma$-hydroxy butyric acid, $\delta$-valerolactone, $\delta$-hydroxy valeric acid, hydroxybutyric acids, malic acid, or mixtures thereof; wherein at least one of component (a) is soluble in an aqueous solution and miscible with component (b), the weight ratio of component (a) to component (b) is within the range of 2:1 to 1:99, the composition can be reconstituted in water or an aqueous solution to form a homogeneous solution or a uniform colloidal system, the composition is free of toxic or dangerous organic solvents, and the composition possesses reverse thermal gelation properties such that it forms a gel when reconstituted and administered to a warm blooded mammal.

2. The composition according to claim 1 wherein the PEG derivative is an ortho ester derivatized PEG.

3. The composition according to claim 1 wherein the PEG derivative is represented by $R^1$—CO—O—($CH_2$—$CH_2$—O)$_n$—CO—$R^2$ or $R^1$—O—($CH_2$—$CH_2$—O)$_n$—$R^2$, —wherein $R^1$ and $R^2$ are independently H or $C_1$ to $C_{10}$ alkyl and n is an integer between 3 and 20.

4. The composition according to claim 1 further comprising a drug.

5. The composition according to claim 4, wherein the drug has limited solubility or dispersibility in an aqueous or hydrophilic environment.

6. The composition according to claim 4, wherein the drug is present at between about $10^{-6}$ to about 100 percent by weight of the combined weight of the block copolymer and the PEG, PEG derivative or mixtures thereof.

7. The composition according to claim 6, wherein the drug is present at between about 0.001% to 25% by weight.

8. The composition of claim 1, wherein said composition can be reconstituted in water or an aqueous solution to form a homogeneous solution or a uniform colloidal system within 0.01 minutes to 120 minutes.

9. The composition of claim 1, wherein said composition can be reconstituted in water or an aqueous solution to form a homogeneous solution or a uniform colloidal system within 0.01 minutes to 60 minutes.

10. The composition of claim 1, wherein said composition can be reconstituted in water or an aqueous solution to form a homogeneous solution or a uniform colloidal system within 0.01 minutes to 30 minutes.

11. The composition of claim 1, wherein the weight ratio of the biodegradable block copolymeric drug carrier and the PEG, PEG derivative or mixtures thereof is within the range of 1:2 to 1:5.

12. The composition of claim 1, wherein the PEG or PEG derivative comprises PEG200NF, PEG300NF, or PEG600NF.

13. The composition of claim 1, wherein the PEG or PEG derivative comprises PEG200NF or PEG300NF.

14. An aqueous composition comprising the composition of claim 1 reconstituted in an aqueous vehicle, wherein said composition is a homogeneous solution or uniform colloidal system, said composition being free of organic solvent.

15. The aqueous composition of claim 14, wherein the aqueous vehicle is water for injection.

16. A method of administration comprising
reconstituting the composition of claim 1 by addition of water or an aqueous solution to form a homogeneous solution or a uniform colloidal system within 0.01 minutes to 120 minutes;
administering the homogeneous solution or uniform colloidal system to a warm blooded mammal, wherein the composition forms a gel when reconstituted and administered to a warm blooded mammal.

17. The method of administration of claim 16, wherein the administering step is through the parenteral route.

18. The method of administration of claim 16, wherein the administering step is by injection.

19. A composition comprising:
(a) one or more biodegradable block copolymer drug carriers comprising A-B, A-B-A or B-A-B block copolymers having a total weight average molecular weight of 2000 to 4990 Daltons, wherein the A block is a biodegradable polyester or poly(ortho ester) and the B block is polyethylene glycol (PEG), and the weight percentage of the A block is between 51% to 83% and the weight percentage of the B block is between 17% to 49%; and
(b) a PEG derivative, or a mixture of PEG and a PEG derivative, said PEG or PEG derivative having a molecular weight of 150 to 1100 Daltons,
wherein the PEG derivative is an ester derivatized PEG and
wherein the PEG is derivatized with D,L-lactide, D-lactide, L-lactide, D,L-lactic acid, D-lactic acid, L-lactic acid, glycolide, glycolic acid, ε-caprolactone, 1,4-dioxan-2-one, ε-hydroxy hexanoic acid, γ-butyrolactone, γ-hydroxy butyric acid, δ-valerolactone, δ-hydroxy valeric acid, hydroxybutyric acids, malic acid, or mixtures thereof;
wherein at least one of component (a) is soluble in an aqueous solution and miscible with component (b), the weight ratio of component (a) to component (b) is within the range of 2:1 to 1:99, the composition can be reconstituted in water or an aqueous solution to form a homogeneous solution or a uniform colloidal system, the composition is free of toxic or dangerous organic solvents, and the composition possesses reverse thermal gelation properties such that it forms a gel when reconstituted and administered to a warm blooded mammal.

\* \* \* \* \*